US008558164B2

(12) United States Patent
Kamimura et al.

(10) Patent No.: US 8,558,164 B2
(45) Date of Patent: Oct. 15, 2013

(54) OPTICAL MEASUREMENT SYSTEM, OPTICAL MEASUREMENT APPARATUS, CALIBRATION MEMBER, AND CALIBRATION METHOD

(71) Applicant: Olympus Medical Systems Corp., Tokyo (JP)

(72) Inventors: Kenji Kamimura, Hachioji (JP); Takeshi Suga, Hino (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 13/651,711

(22) Filed: Oct. 15, 2012

(65) Prior Publication Data

US 2013/0206971 A1   Aug. 15, 2013

Related U.S. Application Data

(63) Continuation of application No. PCT/JP2012/060467, filed on Apr. 18, 2012.

(60) Provisional application No. 61/477,884, filed on Apr. 21, 2011.

(51) Int. Cl.
*G01D 18/00* (2006.01)
*G12B 13/00* (2006.01)
*H05B 33/00* (2006.01)

(52) U.S. Cl.
USPC ............... 250/252.1; 250/484.2; 250/484.5

(58) Field of Classification Search
USPC ............................................ 250/252.1, 458.1
See application file for complete search history.

(56) References Cited

U.S. PATENT DOCUMENTS

| 7,652,881 | B1 | 1/2010 | Sun |
| 2008/0037024 | A1 | 2/2008 | Backman et al. |
| 2009/0003759 | A1 | 1/2009 | Boyd |
| 2009/0009759 | A1 | 1/2009 | Backman et al. |
| 2010/0317919 | A1 | 12/2010 | Takaoka et al. |

FOREIGN PATENT DOCUMENTS

| JP | A-2002-303547 | 10/2002 |
| JP | A-2003-4365 | 1/2003 |
| JP | A-2003-4635 | 1/2003 |
| JP | A-2009-236709 | 10/2009 |
| JP | A-2009-537014 | 10/2009 |
| WO | WO 2007/133684 A2 | 11/2007 |
| WO | WO 2008/050712 A1 | 5/2008 |

OTHER PUBLICATIONS

International Search Report issued in International Application No. PCT/JP2012/060467 dated Jul. 24, 2012.

*Primary Examiner* — David Porta
*Assistant Examiner* — Abra Fein
(74) *Attorney, Agent, or Firm* — Oliff & Berridge, PLC (57) ABSTRACT

An optical measurement system including: a probe including a plurality of light-receiving fibers and an irradiation fiber; a calibration member including a frame member and a fluorescent body provided in an inner side of the frame member to emit fluorescent light using excitation light, the calibration member being used while the fluorescent body surface faces a leading end of the probe; a fluorescence excitation light source that supplies excitation light to the irradiation fiber; a measurement unit that measures each light output from a plurality of the light-receiving fibers; and a calibration processing unit that calibrates the received light intensity between a plurality of the light-receiving fibers based on the measurement result obtained in the measurement unit by measuring light output from a plurality of the light-receiving fibers for fluorescent light from the fluorescent body emitted by irradiation with the excitation light.

14 Claims, 7 Drawing Sheets

OPTICAL MEASUREMENT SYSTEM, OPTICAL MEASUREMENT APPARATUS, CALIBRATION MEMBER, AND CALIBRATION METHOD

CROSS-REFERENCE TO RELATED APPLICATIONS

This application is a continuation of PCT international application Ser. No. PCT/JP2012/060467 filed on Apr. 18, 2012 which designates the United States, incorporated herein by reference, and which claims the benefit of priority from U.S. provisional application No. 61/477,884, filed on Apr. 21, 2011, incorporated herein by reference.

BACKGROUND OF THE INVENTION

1. Field of the Invention

The present invention relates to an optical measurement system for measuring scattering light using a plurality of light-receiving fibers, an optical measurement apparatus, a calibration member used in a calibration process of the optical measurement apparatus, and a calibration method in the optical measurement apparatus.

2. Description of the Related Art

In recent years, there has been proposed an optical measurement apparatus using a low-coherence enhanced backscattering (LEBS) technique for detecting properties of body tissue by irradiation with low-coherent light having a short spatial coherence length onto body tissue, which is a scattering body, from a probe leading end and measuring the intensity distribution of the scattering light (for example, refer to International Patent Publication Pamphlet No. WO2007/133684, U.S. Patent Application Laid-Open No. 2008/0037024, U.S. Pat. No. 7,652,881, and U.S. Patent Application Laid-Open No. 2009/0003759). Such an optical measurement apparatus can perform optical measurement for a measurement target such as body tissue in combination with an endoscope used to observe internal organs such as digestive organs.

The optical measurement apparatus using such the LEBS technique measures the intensity distribution of the scattering light of body tissue by obtaining the scattering light having a plurality of desired angles using a plurality of light-receiving fibers in the probe and obtains a characteristic value regarding properties of body tissue based on the measurement result.

SUMMARY OF THE INVENTION

An optical measurement system according to an aspect of the present invention is for measuring scattering light using a plurality of light-receiving fibers, each of which outputs, from a base end, light incident from a leading end. The optical measurement system includes a probe having the plurality of light-receiving fibers and an irradiation fiber that emits, from a leading end, light supplied from a base end; a calibration member having a fluorescent body that emits fluorescent light using excitation light having a wavelength belonging to a wavelength band different from a scattering light measurement wavelength band, the calibration member being used while the excitation light is in a position to irradiate the fluorescent body; an excitation light source that supplies, to the irradiation fiber, excitation light having a wavelength belonging to a wavelength band different from the scattering light measurement wavelength band; a measurement unit that measures each light output from the plurality of light-receiving fibers; and a calibration processing unit that calibrates a relation of a received light intensity between the plurality of the light-receiving fibers based on a measurement result obtained in the measurement unit by measuring light output from the plurality of the light-receiving fibers for fluorescent light from the fluorescent body emitted by irradiation with the excitation light.

An optical measurement apparatus according to another aspect of the present invention is for performing scattering light measurement using a probe having a plurality of light-receiving fibers each of which outputs, from a base end, light incident from a leading end. The optical measurement apparatus includes an excitation light source that emits excitation light having a wavelength belonging to a wavelength band different from a scattering light measurement wavelength band; a measurement unit that measures each light output from the plurality of the light-receiving fibers; and a calibration processing unit that calibrates a relation of a received light intensity between the plurality of the light-receiving fibers based on the measurement result obtained in the measurement unit by measuring light output from the plurality of the light-receiving fibers for fluorescent light from the fluorescent body emitted by irradiation with the excitation light.

A calibration member according to another aspect of the present invention is used in a calibration process of an optical measurement apparatus for performing scattering light measurement using a probe having a plurality of light-receiving fibers. The calibration member includes scattering particles that have a predetermined scattering characteristic, and a fluorescent body that emits fluorescent light based on excitation light having a wavelength belonging to a wavelength band different from a scattering light measurement wavelength band. The calibration member is used while the excitation light is in a position to irradiate the fluorescent body.

A calibration method according to another aspect of the present invention is performed by an optical measurement apparatus including a measurement unit for performing scattering light measurement using a plurality of light-receiving fibers, each of which outputs, from a base end, light incident from a leading end. The calibration method includes a first measurement step of measuring each light output from the plurality of the light-receiving fibers for fluorescent light emitted by irradiating a fluorescent body with excitation light having a wavelength belonging to a wavelength band different from a scattering light measurement wavelength band by the measurement unit; and a first calibration step of calibrating a relation of a received light intensity between the plurality of the light-receiving fibers based on the measurement result of the first measurement step.

The above and other objects, features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Hereinafter, an optical measurement system, an optical measurement apparatus, a calibration member, and a calibration process according to an exemplary embodiment of the invention will be described in detail with reference to the accompanying drawings. The invention is not limited to the embodiments described below. In the description of drawings, like reference numerals denote like elements. It is noted that the drawings are schematically provided, and the relation of thicknesses and widths of each member and ratios of each member may be different from those of the reality. Among the drawings, a portion having a different relation or ratio in size from that of other drawings may be included.

Figure 1:
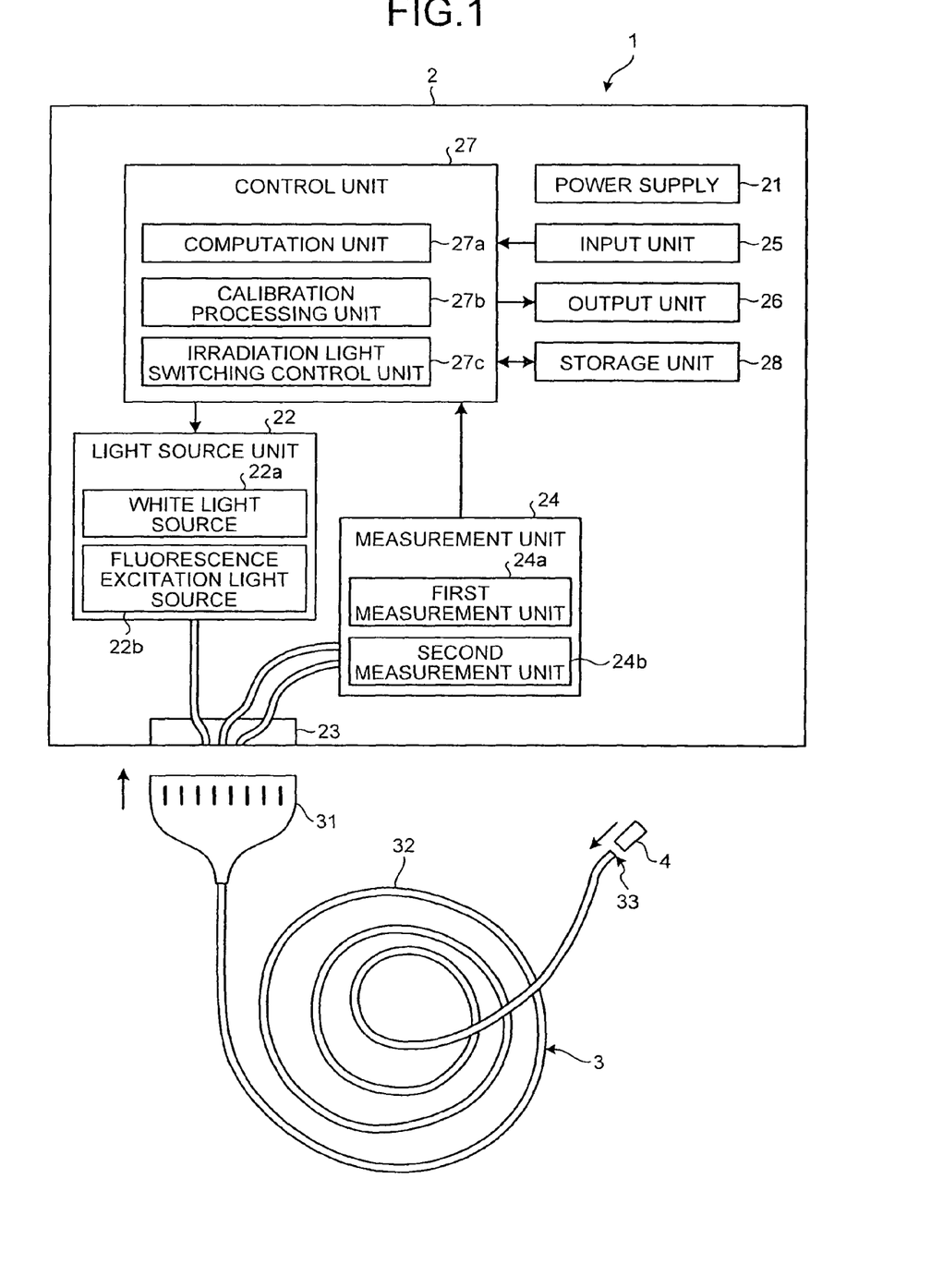
FIG. 1 is a block diagram illustrating a schematic configuration of an optical measurement system according to an embodiment of the invention.
Figure 2:
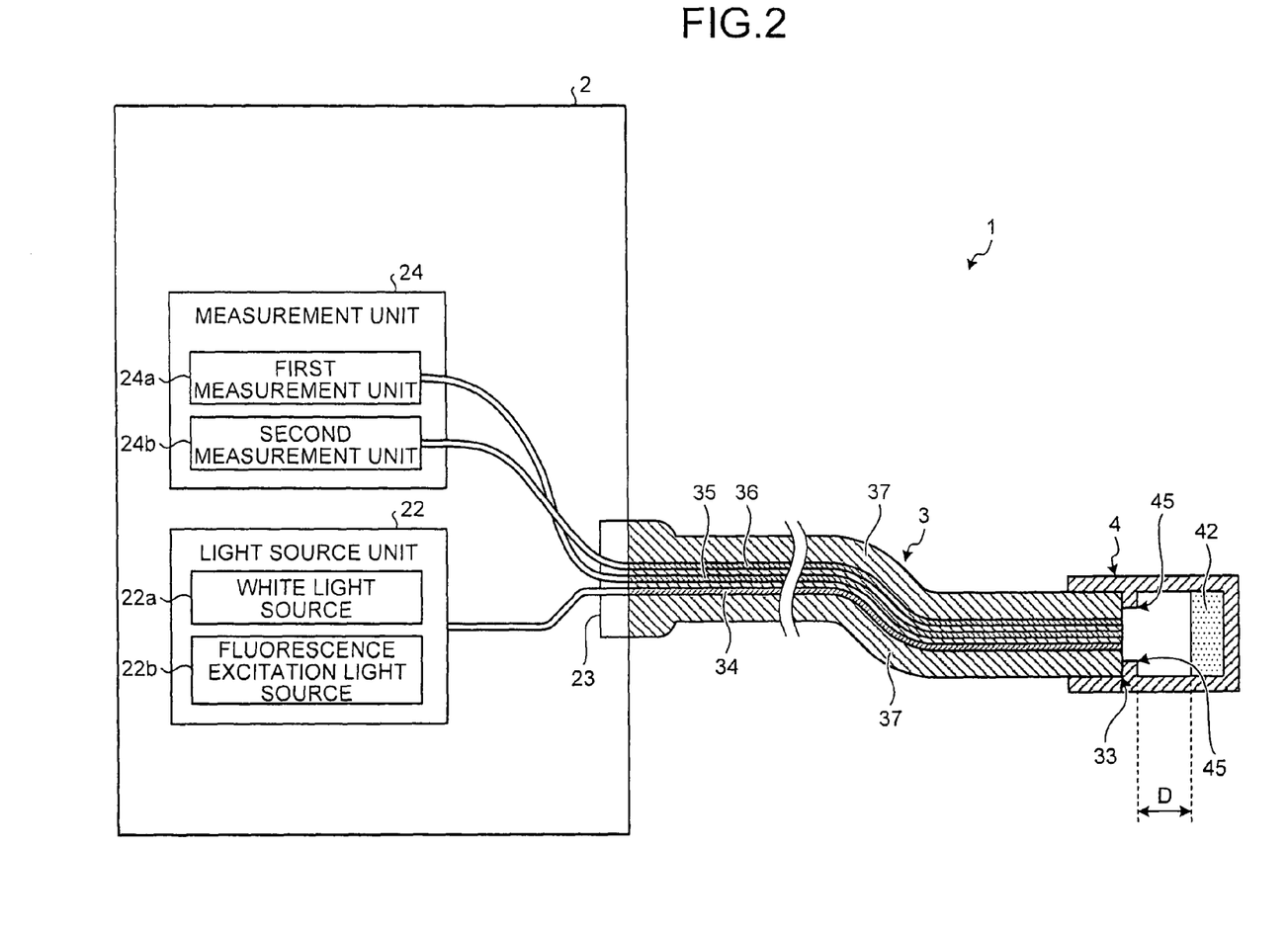
FIG. 2 is a cross-sectional view illustrating main parts of the optical measurement system of FIG. 1.

FIG. 1 is a block diagram illustrating a schematic configuration of the optical measurement system according to an embodiment of the invention. FIG. 2 is a cross-sectional view illustrating main parts of the optical measurement system of FIG. 1. FIG. 2 schematically illustrates main parts of the measurement apparatus of the optical measurement system of FIG. 1 for description purposes.

As illustrated in FIG. 1, an optical measurement system 1 according to an embodiment includes a measurement apparatus 2 that performs optical measurement for a measurement target such as body tissue to detect properties of the measurement target, a probe 3 inserted into a subject, and a calibration member 4 attached to a leading end 33 of a probe 3 during a calibration process in the measurement apparatus 2. In the probe 3, a base end is detachably installed in the measurement apparatus 2. The probe 3 has an irradiation fiber and a plurality of light-receiving fibers. The probe 3 emits, from the leading end to the measurement target, the light supplied from the base end and outputs, from the base end to the measurement apparatus 2, scattering light and reflection light as returned light from the measurement target incident from the leading end.

The measurement apparatus 2 includes a power supply 21, a light source unit 22, a connector 23, a measurement unit 24, an input unit 25, an output unit 26, a control unit 27, and a storage unit 28.

The power supply 21 supplies power to each component of the measurement apparatus 2.

The light source unit 22 emits light to be supplied to the probe 3. The light source unit 22 includes a white light source 22a and a fluorescence excitation light source 22b. The white light source 22a is implemented using a low-coherent light source such as white light-emitting diode (LED), a xenon lamp, and a halogen lamp, and one or more lenses. The white light source 22a supplies the low-coherent light to the probe 3 at a predetermined timing. The fluorescence excitation light source 22b emits light having a wavelength belonging to a wavelength band different from the scattering light measurement wavelength band in the measurement unit 24 to serve as excitation light for exciting fluorescent particles of the calibration member 4 as described below.

The connector 23 is used to detachably connect the base end of the probe 3 to the measurement apparatus 2. Through the connector 23, the light emitted from the light source unit 22 is supplied to the probe 3, and the returned light output from the probe 3 is output to the measurement unit 24.

The measurement unit 24 measures the returned light from the body tissue which is the light output from the probe 3. The measurement unit 24 is realized using a spectroscope. The measurement unit 24 measures, for example, the spectral component and the intensity of the returned light output from the probe 3 to perform measurement for each wavelength. The measurement unit 24 outputs the measurement result to the control unit 27. The measurement unit 24 repeatedly performs the returned light measurement process at a predetermined measurement timing corresponding to the light-emitting process of the light source unit 22. Measurement devices of the measurement unit 24 are provided for each of light-receiving fibers 35 and 36 of the probe 3 described below (refer to FIG. 2). In the example of FIG. 1, the measurement unit 24 includes two spectroscopes, a first measurement unit 24a and a second measurement unit 24b.

The input unit 25 is realized using a push-type switch and the like. The input unit 25 receives instruction information for instructing activation of the measurement apparatus 2 or various other types of instruction information and inputs the information to the control unit 27 by manipulating a switch and the like.

The output unit 26 outputs information regarding various processes in the optical measurement system 1. The output unit 26 is realized using a display, a loudspeaker, a motor, and the like so that information regarding various processes in the optical measurement system 1 is output by outputting image information, audio information, or vibration.

The control unit 27 controls processing operations of each component of the measurement apparatus 2. The control unit 27 is realized using a central processing unit (CPU) and a semiconductor memory such as a random access memory (RAM). The control unit 27 controls operations of the measurement apparatus 2 by transferring instruction information or data to each component of the measurement apparatus 2 and the like. The control unit 27 includes a computation unit 27a, a calibration processing unit 27b, and an irradiation light switching control unit 27c.

The computation unit 27a performs plural kinds of computation processes based on the measurement result of the measurement unit 24 to compute the characteristic value regarding properties of body tissue. The type of the characteristic value that is computed by the computation unit 27a and serves as an obtainment target is set, for example, based on instruction information input from the input unit 25 by an operator's manipulation.

The calibration processing unit 27b controls the light source unit 22 and the measurement unit 24 to perform the calibration process for the measurement apparatus 2 for guaranteeing detection accuracy before the measurement target detection starts. The calibration process is performed whenever the probe 3 is replaced.

The irradiation light switching control unit 27c performs control for switching the light source for actually emitting light between the white light source 22a and the fluorescence excitation light source 22b in the light source unit 22. The irradiation light switching control unit 27c causes the white light source 22a to perform the irradiation process when the scattering light measurement for the measurement target is performed. The irradiation light switching control unit 27c causes either the white light source 22a or the fluorescence excitation light source 22b to perform the irradiation process depending on the content of the calibration process when the calibration process is performed.

The storage unit 28 stores an optical measurement program for causing the measurement apparatus 2 to execute the optical measurement process and various types of information regarding the optical measurement process. The storage unit 28 stores the characteristic value computed by the computation unit 27a. The storage unit 28 stores a calibration program for causing the measurement apparatus 2 to execute the calibration process and various types of information regarding the calibration process.

The probe 3 is realized using a plurality of optical fibers. The probe 3 includes a base end portion 31 detachably connected to the connector 23 of the measurement apparatus 2, a flexible portion 32 that is flexible, and a leading end 33 that emits the light supplied from the light source unit 22 and receives the scattering light from the measurement target. In using the LEBS technique, a plurality of light-condensing fibers are provided to condense each of at least two scattering light beams having different scattering angles. Specifically, as illustrated in FIG. 2, the probe 3 includes an irradiation fiber 34 that irradiates the measurement target from the leading end with the light from the light source unit 22 supplied from the base end, and two light-receiving fibers 35 and 36 that output, from the base end, scattering light and reflection light having different scattering angles from the measurement target, incident from the leading end. The side surface of the irradiation fiber 34 and the side surfaces of the light-receiving fibers 35 and 36 are covered by a cover portion 37. The optical measurement apparatus 1 is used, for example, in combination with an endoscope system that observes internal organs such as digestive organs, so that the probe 3 is introduced into an inner side of a subject via an endoscope probe channel inserted into a subject.

Figure 3:
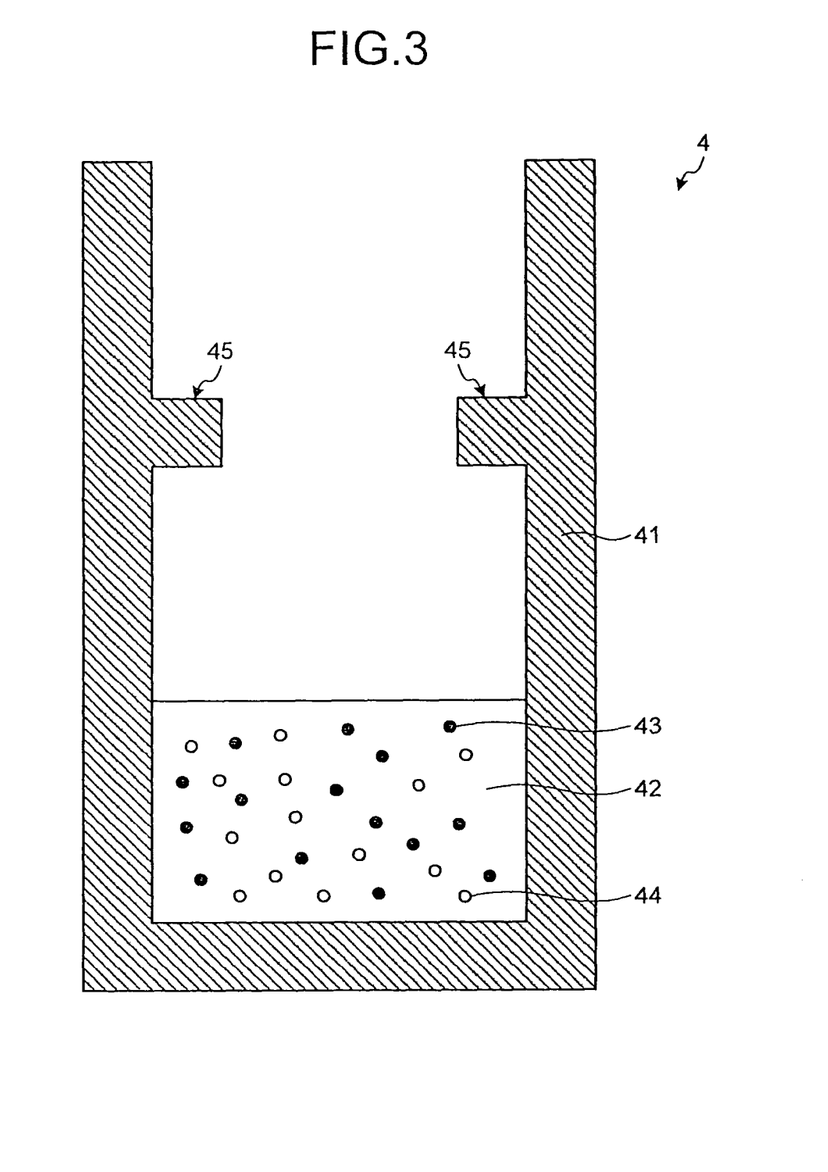
FIG. 3 is a cross-sectional view illustrating the calibration member of FIGS. 1 and 2.

The optical measurement system 1 performs the calibration process before the measurement is initiated while the leading end 33 of the probe 3 is covered by the calibration member 4. FIG. 3 is a cross-sectional view illustrating the calibration member 4 of FIGS. 1 and 2.

As illustrated in FIGS. 2 and 3, the calibration member 4 has a configuration in which a solid medium 42 is provided in an inner side of a main body frame 41 having a cap shape that covers the leading end 33 of the probe 3. Inside the medium 42, scattering particles 43 and fluorescent particles 44 are distributed. The medium 42 is, for example, a transparent solid such as silicon resin, polyethylene resin, gelatin, acrylic resin, and polyamide and is formed of particles sufficiently larger than the scattering particles 43 and the fluorescent particles 44. The scattering particles 43 are, for example, polystyrene particles, alumina fine particles.

Figure 4:
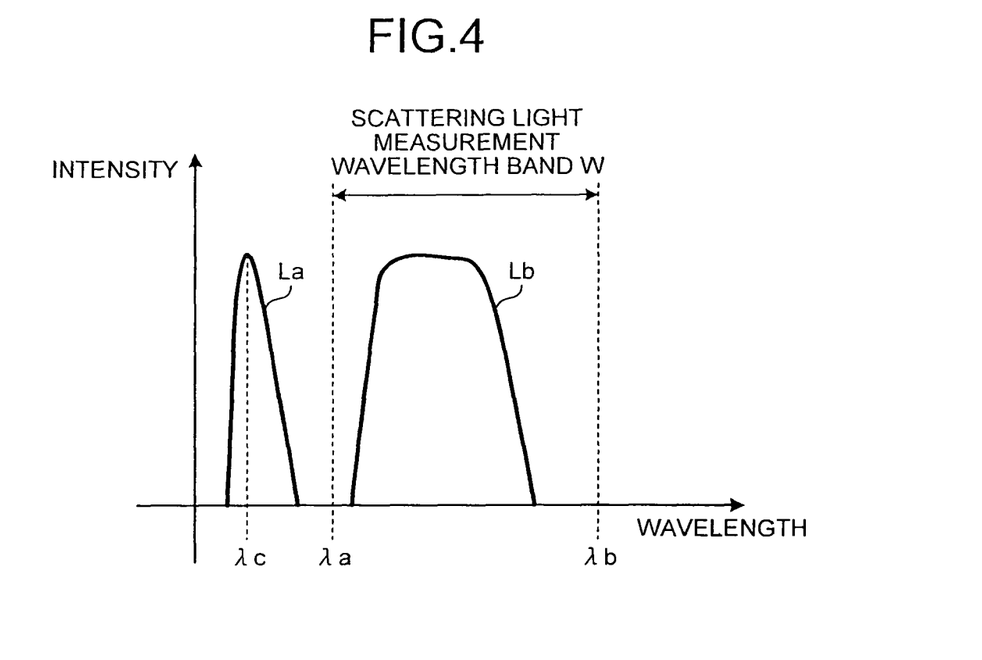
FIG. 4 is a diagram illustrating a fluorescence characteristic of fluorescent particles of FIG. 3.

The fluorescent particle 44 emits fluorescent light having a wavelength longer than that of the excitation light when the excitation light belonging to a predetermined wavelength band is emitted. FIG. 4 is a diagram illustrating a fluorescence characteristic of the fluorescent particle 44 of FIG. 3. The measurement unit 24 performs a spectroscopic process using a scattering light measurement wavelength band W from wavelength $\lambda a$ to wavelength $\lambda b$. If the fluorescent particle 44 is excited by the light of a wavelength $\lambda c$ belonging to a wavelength band different from the scattering light measurement wavelength band W of the measurement unit 24, the fluorescent particle 44 emits fluorescent light having a wavelength belonging to the wavelength band indicated by the curve Lb, and which is included in the scattering light measurement wavelength band W of the measurement unit 24. For this reason, the fluorescence excitation light source 22b emits excitation light of a wavelength band having a peak at a wavelength $\lambda c$, for example, as illustrated in the curve La. A relation between the intensity of the excitation light incident to the fluorescent particle 44 of the calibration member 4 and the intensity of the fluorescent light emitted by the fluorescent particle 44 is obtained in advance.

When the light of a wavelength other than the excitation wavelength band is emitted, the fluorescent particle 44 serves as a scattering body similarly to the scattering particle 43. The scattering particle 43 and the fluorescent particle 44 have a predetermined scattering characteristic and a reflection characteristic, and a wavelength distribution state of the returned light scattered and reflected depending on the incident white light is obtained in advance. Materials or particle sizes of the medium 42, the scattering particle 43, and the fluorescent particle 44 are set based on a relation between wavelengths of the incident light and the returned light and particles.

In order to perform the calibration process stably under a certain condition, the main body frame 41 of the calibration member 4 internally includes a protrusion-shaped stopper 45 for engaging the surface of the cover portion 37 and the calibration member 4 such that the leading end 33 of the probe 3 and the surface of the medium 42 face each other with a certain distance D (refer to FIG. 2). The distance D is set such that the light from the irradiation fiber 34 is incident to the medium 42 in a sufficiently widened state.

The calibration processing unit 27b calibrates a relation of the received light intensity between a plurality of light-receiving fibers 35 and 36 based on the measurement result of the measurement unit 24 for the light output from the plurality of light-receiving fibers 35 and 36 caused by the fluorescent light from the fluorescent particles 44 emitted by irradiation with the excitation light. In addition, the calibration processing unit 27b calibrates the spectral sensitivities of the first and second measurement units 24a and 24b of the measurement unit 24 based on the measurement result of the measurement unit 24 for the reflection light and the scattering light from the scattering particles 43 and the fluorescent particles 44 caused by irradiation with the white light.

Figure 5:
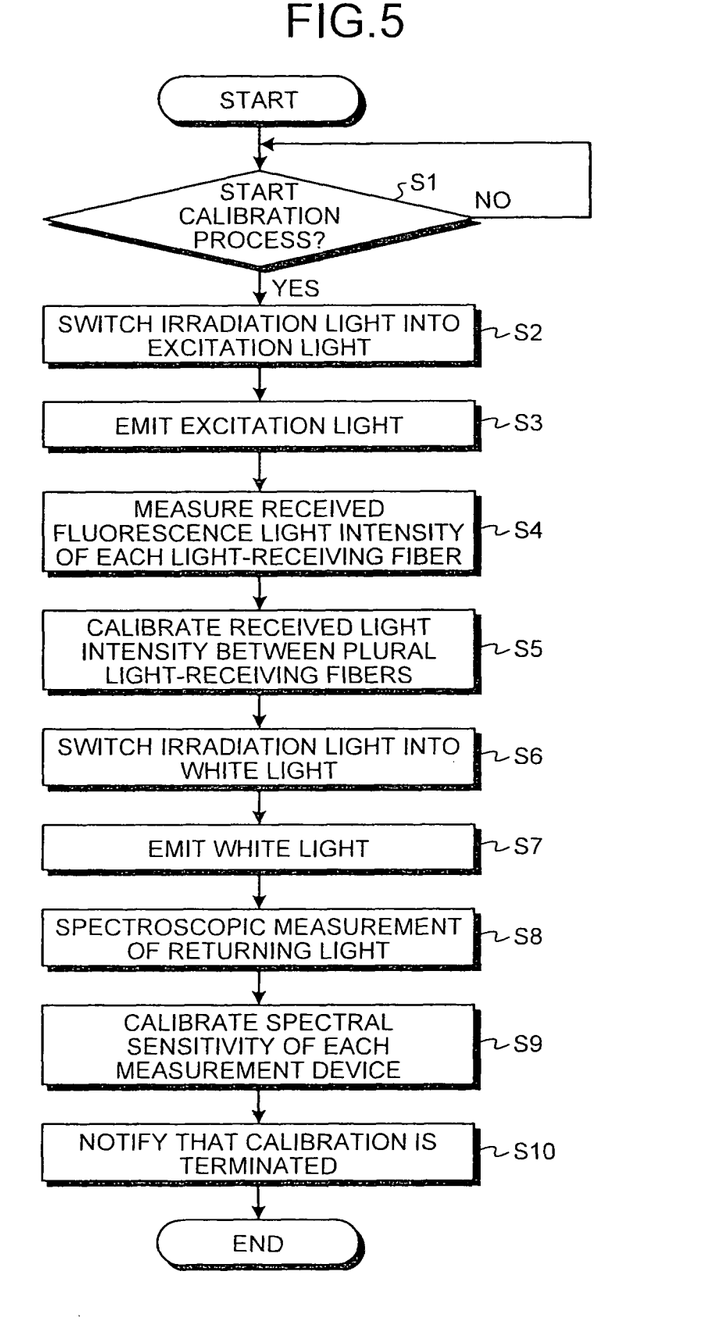
FIG. 5 is a flowchart illustrating a processing sequence of the calibration process in the optical measurement system of FIG. 1.

Next, a calibration process in the optical measurement system 1 will be described. FIG. 5 is a flowchart illustrating a processing sequence of the calibration process in the optical measurement system 1 of FIG. 1. In FIG. 5, a case where the calibration process is subsequently performed after the measurement result for calibration is obtained will be exemplarily described.

As illustrated in FIG. 5, first, the control unit 27 determines whether initiation of the calibration process is instructed (step S1). The control unit 27 determines that initiation of the calibration process is instructed when instruction information for instructing initiation of the calibration process is input from the input unit 25 or when replacement of the probe 3 is detected. If it is determined that initiation of the calibration process is not instructed (NO in step S1), the control unit 27 returns to step S1, so that the determination process of step S1 is repeated until initiation of the calibration process is instructed.

When the control unit 27 determines that initiation of the calibration process is instructed (YES in step S1), the calibration processing unit 27b performs the calibration process for calibrating a relation of the received light intensity between a plurality of light-receiving fibers 35 and 36. First, the irradiation light switching control unit 27c switches the use light source into the fluorescence excitation light source 22b and switches the irradiation light into the excitation light under control of the calibration processing unit 27b (step S2). Subsequently, the calibration processing unit 27b causes the fluorescence excitation light source 22b to emit the excitation light having a peak at a wavelength $\lambda c$ with a predetermined intensity (step S3). The excitation light emitted from the fluorescence excitation light source 22b is emitted through the leading end of the irradiation fiber 34 of the probe 3 to the inner side of the calibration member 4. As a result, the fluorescent particle 44 of the calibration member 4 emits fluorescent light. The fluorescent light from the fluorescent particle 44 does not exhibit coherence and is diffused and radiated. That is, the fluorescent light having a certain intensity depending on the excitation light is incident to each of the light-receiving fibers 35 and 36 without influence of interference.

The measurement unit 24 measures the received light intensity of the fluorescent light of each of the light-receiving fibers 35 and 36 (step S4). In the example of FIG. 2, the first measurement unit 24a measures the received light intensity in the light-receiving fiber 35, and the second measurement unit 24b measures the received light intensity in the light-receiving fiber 36.

Subsequently, the calibration processing unit 27b calibrates a relation of the received light intensity between the light-receiving fibers 35 and 36 based on the measurement result of the received light intensity caused by the measurement unit 24 of each of the light-receiving fibers 35 and 36 (step S5). In this case, the fluorescent light having a certain intensity is incident to each of the light-receiving fibers 35 and 36. For this reason, the calibration processing unit 27b calibrates a ratio of the received light intensity of each of the light-receiving fibers 35 and 36 measured by the measurement unit 24 to match the fluorescent light intensity actually incident to each of the light-receiving fibers 35 and 36. In this manner, the calibration processing unit 27b calibrates the relation of the received light intensity between each of the light-receiving fibers 35 and 36 based on the fluorescent light from the fluorescent particle 44 of the calibration member 4 for the excitation light.

After step S5 is terminated, the calibration processing unit 27b performs a calibration process for calibrating the spectral sensitivity of the first and second measurement units 24a and 24b of the measurement unit 24. First, under control of the calibration processing unit 27b, the irradiation light switching control unit 27c switches the use light source into the white light source 22a and switches the irradiation light into the white light (step S6). Subsequently, the calibration processing unit 27b causes the white light source 22a to emit the white light using a predetermined condition (step S7). The white light emitted from the white light source 22a is emitted through the leading end of the irradiation fiber 34 of the probe 3 into the inner side of the calibration member 4. As a result, the light is scattered and reflected by the scattering particles 43 and the fluorescent particles 44 of the calibration member 4 serving as a scattering body, and certain scattering light and reflection light corresponding to the incident white light are incident to each of the light-receiving fibers 35 and 36 as the returned light.

The first and second measurement units 24a and 24b of the measurement unit 24 perform the spectroscopic measurement for the returned light of each of the light-receiving fibers 35 and 36 (step S8). In this case, for the white light emitted under a certain condition, the returned light having a certain wavelength distribution is incident to the light-receiving fibers 35 and 36. Such a wavelength distribution of the returned light is obtained in advance. The calibration processing unit 27b compares the wavelength distribution of the returned light obtained in advance and actual spectroscopic measurement results of the first and second measurement units 24a and 24b to calibrate the spectral sensitivity of each measurement device of the first and second measurement units 24a and 24b (step S9). In this manner, the calibration processing unit 27b calibrates the spectral sensitivity of each measurement device based on the returned light from the calibration member 4 for the white light.

After step S9 is terminated, the control unit 27 notifies the output unit 26 of a fact that the calibration process is terminated (step S10) and terminates the calibration process. Incidentally, either the calibration process for the received light intensity between the light-receiving fibers 35 and 36 or the calibration process for the spectral sensitivity of the first and second measurement units 24a and 24b may be performed first. For this reason, it may be possible to exchange steps S2 to S5 to steps S6 to S9.

In this manner, in the optical measurement system 1 according to an embodiment, the calibration member 4 having both the scattering characteristic and the fluorescence characteristic is used. In the optical measurement system 1, the calibration for the relation of the received light intensity between the light-receiving fibers 35 and 36 is performed based on the fluorescent light emitted from the fluorescent body by irradiation with the excitation light, and the calibration for the spectral sensitivity of the measurement unit 24 is performed based on the returned light from the scattering body for the white light. Therefore, it is possible to accurately execute both the calibration for the light-receiving fibers 35 and 36 and the calibration for the measurement unit 24.

In addition, in the optical measurement system 1, it is possible to execute both the calibration for the relation of the received light intensity of the light-receiving fibers 35 and 36 and the calibration for the spectral sensitivity of the measurement unit 24 using a single calibration member 4 just by providing the fluorescence excitation light source 22b in the light source unit 22. For this reason, in the optical measurement system 1, it is not necessary to prepare a separate diffusing light source for the calibration process. Therefore, it is possible to execute the calibration process using a simple configuration. Furthermore, in the optical measurement system 1, it is not necessary to replace the calibration member to match the contents of the calibration process. Therefore, it is possible to execute the calibration process simply without performing a cumbersome process.

In addition, in the optical measurement system 1, since the calibration member 4 obtained by distributing scattering particles 43 and fluorescent particles 44 in the solid medium 42 is used, it is possible to appropriately execute the calibration process regardless of where the leading end 33 of the probe 3 and the calibration member 4 are directed.

Although a case where the stopper 45 is provided in an inner side of the main body frame 41 as a calibration member has been exemplarily described in the embodiment, the invention is not limited thereto. For example, a protrusion may be provided in the lateral leading end portion of the cover portion 37, and a trench where the protrusion passes may be provided in an internal wall of the main body frame of the calibration member such that the leading end 33 of the probe 3 faces the surface of the medium 42 with a certain distance D (refer to FIG. 2). The trench provided in the internal wall of the main body of the calibration member extends downwardly up to an intermediate portion of the internal wall corresponding to the distance D from the upper portion.

Although description has been made in the embodiment for a configuration in which, both the scattering particles 43 and the fluorescent particles 44 are distributed in the medium 42 as the calibration member as illustrated in FIG. 3, only the fluorescent particles 44 may be distributed in the medium 42 because the fluorescent particles 44 serve as a scattering body.

Figure 6:
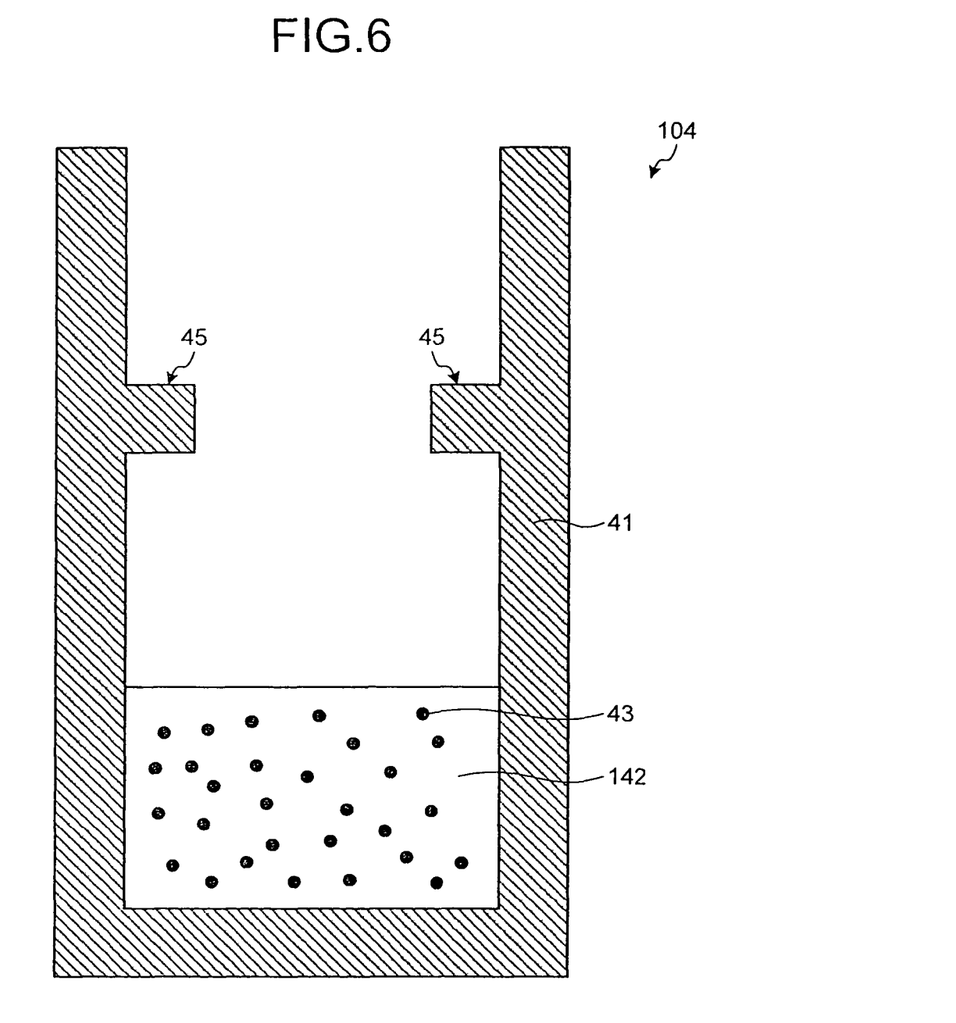
FIG. 6 is a cross-sectional view illustrating another example of the calibration member of FIG. 1.

Although description has been made in the embodiment for a configuration in which the scattering particles 43 are distributed in the medium 42 as a calibration member, the invention is not limited thereto. In a calibration member 104, as illustrated in FIG. 6, a fluorescent body 142 may be used as a medium having the scattering particles 43 distributed therein, which is formed by distributing the scattering particles 43 in an inner side of the fluorescent body 142. In this case, the fluorescent body 142 is a solid capable of transmitting visible light rays. Similarly, in this case, a stopper 45 is provided in the calibration member 104 such that the leading end 33 of the probe 3 faces the surface of the solid fluorescent body 142 with a certain distance.

Figure 7:
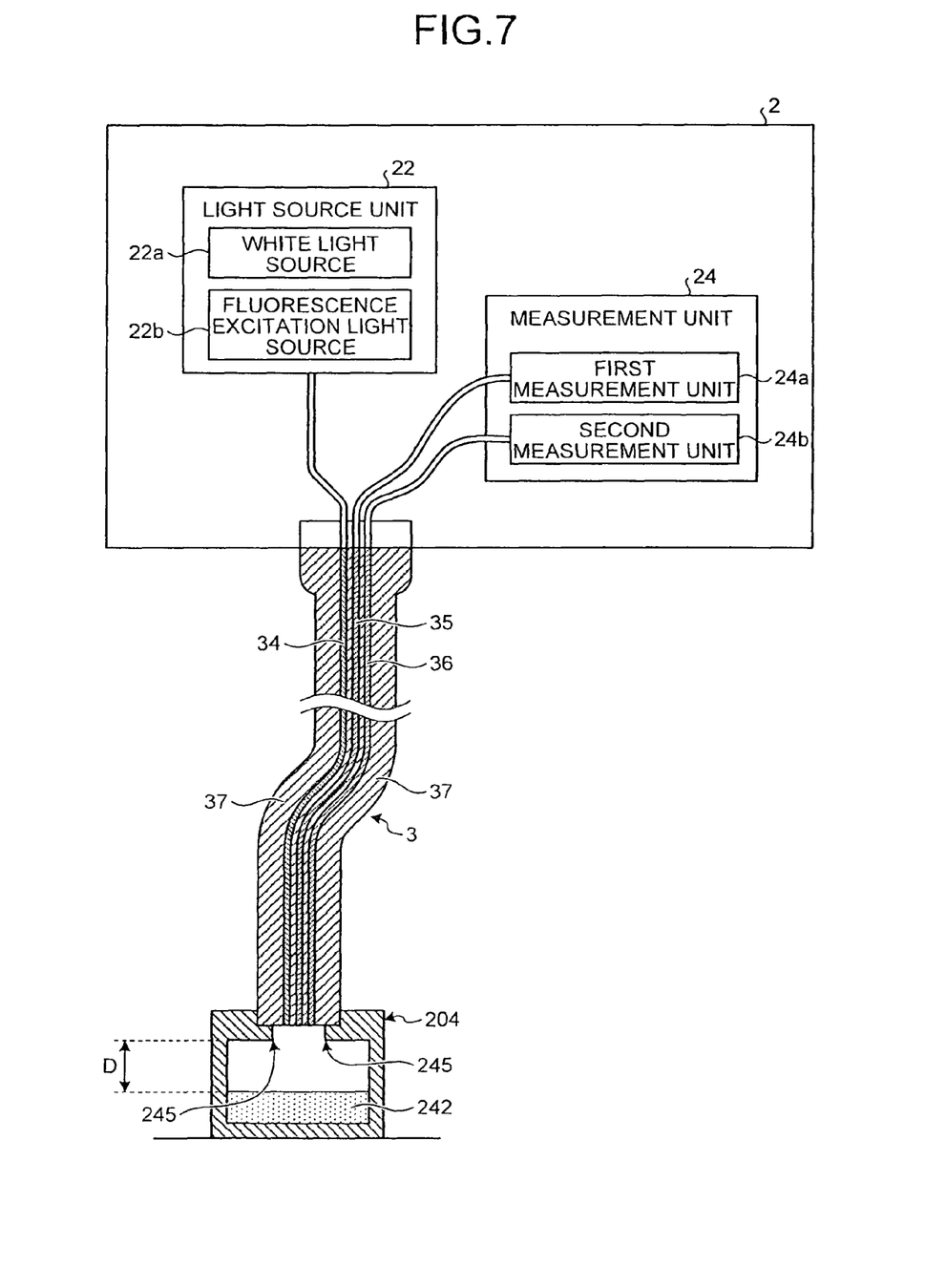
FIG. 7 is a cross-sectional view illustrating another example of the calibration member of FIG. 1.

Although description has been made in the embodiment for a configuration in which the scattering particles 43 are distributed in an inner side of the solid medium 42 or the fluorescent body 142 as the calibration member, the medium 42 or the fluorescent body 142 is not necessarily a solid. As illustrated in FIG. 7, if a calibration member 204 can be provided on a horizontal plane, a liquid or gelatinous medium 242 may be used. Similarly, in this case, a stopper 245 is provided in the main body frame of the calibration member 204 such that the leading end of the probe 3 faces the surface of the medium 242 with a certain distance D when the calibration member 204 is provided on a horizontal plane.

Although description has been made in the embodiment for a configuration in which the fluorescence excitation light source 22b is provided in addition to the white light source 22a, the invention is not limited thereto. A movable filter that transmits only the excitation wavelength light for the fluorescent body provided in the calibration members 4, 104, and 204 may be provided in addition to the white light source 22a. In this case, the irradiation light switching control unit 27c may place this filter in the middle of the optical path of white light from the white light source 22a when a relation of the received light intensity between a plurality of light-receiving fibers is calibrated. In addition, the irradiation light switching control unit 27c may retreat the filter from the optical path of the white light from the white light source 22a when the spectral sensitivity of the first and second measurement units 24a and 24b of the measurement unit 24 is calibrated, and a measurement process for obtaining the characteristic value is performed.

Although description has been made for a case where the calibration process is performed after the calibration measurement result is obtained according to the present embodiment, the calibration process may be performed after the measurement for obtaining the characteristic value if the calibration measurement result has been obtained.

What is claimed is:

1. An optical measurement system for measuring scattering light using a plurality of light-receiving fibers, each of which outputs, from a base end, light incident from a leading end, the optical measurement system comprising:
    a probe having the plurality of light-receiving fibers and an irradiation fiber that emits, from a leading end, light supplied from a base end;
    a calibration member having a fluorescent body that emits fluorescent light using excitation light having a wavelength belonging to a wavelength band different from a scattering light measurement wavelength band, the calibration member being used while the excitation light is in a position to irradiate the fluorescent body;
    an excitation light source that supplies, to the irradiation fiber, excitation light having a wavelength belonging to a wavelength band different from the scattering light measurement wavelength band;
    a measurement unit that measures each light output from the plurality of the light-receiving fibers; and
    a calibration processing unit that calibrates a relation of a received light intensity between the plurality of the light-receiving fibers based on a measurement result obtained in the measurement unit by measuring light output from the plurality of the light-receiving fibers for fluorescent light from the fluorescent body emitted by irradiation with the excitation light.

2. The optical measurement system according to claim 1, further comprising a white light source that supplies white light to the irradiation fiber,
    wherein the calibration member further includes scattering particles having a predetermined scattering characteristic, and
    the calibration processing unit calibrates spectral sensitivity of the measurement unit based on the measurement result obtained in the measurement unit by measuring reflection light and/or scattering light from the scattering particles by irradiation with the white light.

3. The optical measurement system according to claim 2, wherein the fluorescent body has a granular shape, and the scattering particles and the fluorescent body are distributed in a predetermined medium provided in an inner side of a frame member.

4. The optical measurement system according to claim 3, wherein the frame member includes an engagement portion for engaging the probe and the calibration member such that a leading end of the probe faces a surface of the medium with a certain distance.

5. The optical measurement system according to claim 3, wherein the predetermined medium is a solid, and the frame member has a cap shape for covering a leading end of the probe.

6. The optical measurement system according to claim 1, wherein the fluorescent body is provided in an inner side of a frame member and is a medium in which scattering particles are distributed.

7. The optical measurement system according to claim 6, wherein the frame member includes an engagement portion for engaging the probe and the calibration member such that a leading end of the probe faces a surface of the fluorescent body with a certain distance.

8. The optical measurement system according to claim 6, wherein the fluorescent body is a solid, and the frame member has a cap shape for covering a leading end of the probe.

9. An optical measurement apparatus for performing scattering light measurement using a probe having a plurality of light-receiving fibers, each of which outputs light incident from a leading end through a base end, and having an irradiation fiber that emits light supplied from the base end through the leading end, the optical measurement apparatus comprising:
    an excitation light source that supplies excitation light having a wavelength belonging to a wavelength band different from a scattering light measurement wavelength band, to the irradiation fiber;
    a measurement unit that measures each light output from the plurality of the light-receiving fibers; and
    a calibration processing unit that calibrates a relation of a received light intensity between the plurality of the light-receiving fibers based on the measurement result obtained in the measurement unit by measuring light output from the plurality of the light-receiving fibers for fluorescent light from the fluorescent body emitted by irradiation with the excitation light.

10. The optical measurement apparatus according to claim 9, further comprising a white light source that supplies white light to the irradiation fiber, wherein the calibration processing unit calibrates spectral sensitivity of the measurement unit based on the measurement result obtained in the measurement unit by measuring reflection light and/or scattering light from scattering particles having a predetermined scattering characteristic by irradiation with the white light.

11. A calibration member used in a calibration process of an optical measurement apparatus for performing scattering light measurement using a probe having a plurality of light-receiving fibers, the calibration member comprising:

scattering particles having specified scattering characteristics;

a fluorescent body that has a granular shape and emits fluorescent light based on excitation light having a wavelength in a wavelength band different from a scattering light measurement wavelength band; and a frame member that has a cap shape for covering a leading end of the probe, wherein the scattering particles and the fluorescent body and distributed in a predetermined medium provided in an inner side of the frame member, the predetermined medium is a solid, and excitation light is used when irradiating the fluorescent body.

12. A calibration member used in a calibration process of an optical measurement apparatus for performing scattering light measurement using a probe having a plurality of light-receiving fibers, the calibration member comprising:

scattering particles having specified scattering characteristics;

a fluorescent body that emits fluorescent light based on excitation light having a wavelength in a wavelength band different from a scattering light measurement wavelength band; and a frame member that has a cap shape for covering a leading end of the probe, wherein the fluorescent body is provided in an inner side of the frame member, the fluorescent body is a solid medium in which the scattering particles are distributed, and the excitation light is used when irradiating the fluorescent body.

13. A calibration method of an optical measurement apparatus including a measurement unit for performing scattering light measurement using a plurality of light-receiving fibers, each of which outputs, from a base end, light incident from a leading end, the calibration method comprising:

a first measurement step of measuring each light output from the plurality of the light-receiving fibers for fluorescent light emitted by irradiating a fluorescent body with excitation light having a wavelength belonging to a wavelength band different from a scattering light measurement wavelength band by the measurement unit; and a first calibration step of calibrating a relation of a received light intensity between the plurality of the light-receiving fibers based on the measurement result of the first measurement step.

14. The calibration method according to claim 13, further comprising:

a second measurement step of measuring reflection light and/or scattering light from scattering particles having a predetermined scattering characteristic for irradiation with white light by the measurement unit; and a second calibration step of calibrating spectral sensitivity of the measurement unit based on the measurement result of the second measurement step.

* * * * *